(12) United States Patent
Jansen et al.

(10) Patent No.: US 10,206,859 B2
(45) Date of Patent: *Feb. 19, 2019

(54) COSMETIC COMPOSITION

(71) Applicant: The Procter & Gamble Company, Cincinnati, OH (US)

(72) Inventors: Joseph Harry Jansen, Harrison, OH (US); Paul Robert Tanner, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 442 days.

This patent is subject to a terminal disclaimer.

(21) Appl. No.: 14/445,456

(22) Filed: Jul. 29, 2014

(65) Prior Publication Data

US 2016/0030313 A1 Feb. 4, 2016

(51) Int. Cl.
*A61K 8/37* (2006.01)
*A61K 8/06* (2006.01)
*A61K 8/02* (2006.01)
*A61K 8/73* (2006.01)
*A61Q 19/00* (2006.01)
*A61Q 17/04* (2006.01)
*A61K 8/891* (2006.01)
*A61K 8/895* (2006.01)

(52) U.S. Cl.
CPC ............... *A61K 8/37* (2013.01); *A61K 8/025* (2013.01); *A61K 8/062* (2013.01); *A61K 8/732* (2013.01); *A61K 8/891* (2013.01); *A61K 8/895* (2013.01); *A61Q 17/04* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 3,755,560 A | 8/1973 | Dickert | |
| 4,421,769 A | 12/1983 | Dixon | |
| 5,041,281 A * | 8/1991 | Strobridge | A61K 8/06 424/59 |
| 5,223,559 A | 6/1993 | Arraudeau | |
| 5,871,761 A | 2/1999 | Kuwata et al. | |
| 5,871,791 A | 2/1999 | Noble | |
| 6,367,484 B1 | 4/2002 | Ramin | |
| 6,531,116 B1 | 3/2003 | Utecht | |
| 6,780,422 B2 | 8/2004 | Brieva et al. | |
| 6,872,401 B2 | 3/2005 | Seyler | |
| 7,172,754 B1 * | 2/2007 | Rosevear | A61K 8/06 424/400 |
| 7,351,417 B2 | 4/2008 | Barrow et al. | |
| 8,425,884 B2 | 4/2013 | Takakura et al. | |
| 9,757,325 B2 | 9/2017 | Alard et al. | |
| 2002/0193513 A1 | 12/2002 | Bara | |
| 2003/0031642 A1 | 2/2003 | Lezer | |
| 2003/0049212 A1 | 3/2003 | Robinson | |
| 2003/0095941 A1 | 5/2003 | Anderson | |
| 2004/0086473 A1 | 5/2004 | Rabe | |
| 2004/0086474 A1 | 5/2004 | Rabe | |
| 2004/0185070 A1 | 9/2004 | Barrow et al. | |
| 2004/0228819 A1 | 11/2004 | Rabe | |
| 2005/0058677 A1 | 3/2005 | Ricard | |
| 2005/0058678 A1 | 3/2005 | Ricard | |
| 2006/0057127 A1 | 3/2006 | Liu | |
| 2006/0057217 A1 | 3/2006 | Utschig et al. | |
| 2006/0257346 A1 | 11/2006 | Mohammadi | |
| 2007/0059262 A1 | 3/2007 | Taniguchi | |
| 2007/0065381 A1 | 3/2007 | Elsbrock et al. | |
| 2007/0224141 A1 | 9/2007 | Themens | |
| 2007/0237730 A1 | 10/2007 | Polonka | |
| 2008/0145435 A1 | 6/2008 | Ricard | |
| 2008/0181956 A1 | 7/2008 | Ha | |
| 2009/0148393 A1 | 6/2009 | Maitra | |
| 2009/0208443 A1 | 8/2009 | Polonka | |
| 2010/0266651 A1 * | 10/2010 | Czech | A61K 8/893 424/401 |
| 2010/0322983 A1 | 12/2010 | Griffiths | |
| 2013/0095324 A1 * | 4/2013 | Inokuchi | C08J 3/126 428/405 |
| 2013/0243835 A1 | 9/2013 | Tanner et al. | |

(Continued)

FOREIGN PATENT DOCUMENTS

DE 10157490 6/2003
EP 1513491 B1 3/2005

(Continued)

OTHER PUBLICATIONS

"Prime & Anti-Shine Balm" GNPD Nov. 1, 2013; Record ID 2247832.
U.S. Appl. No. 14/596,360, filed Jan. 14, 2015, Joseph Harry Jansen.
U.S. Appl. No. 14/596,363, filed Jan. 14, 2015, Joseph Harry Jansen.
U.S. Appl. No. 14/596,374, filed Jan. 14, 2015, Joseph Harry Jansen.
U.S. Appl. No. 14/596,379, filed Jan. 14, 2015, Joseph Harry Jansen.
U.S. Appl. No. 14/245,230, filed Apr. 4, 2014, Joseph Harry Jansen.
U.S. Appl. No. 14/245,241, filed Apr. 4, 2014, Joseph Harry Jansen.
U.S. Appl. No. 14/445,434, filed Jul. 29, 2014, Joseph Harry Jansen.

(Continued)

Primary Examiner — Monica A Shin
(74) Attorney, Agent, or Firm — John G. Powell

(57) ABSTRACT

A finisher composition in the form of an oil-in-water emulsion. The continuous aqueous phase of the emulsion is from about 20 to 85 wt % of water. The dispersed oil phase of the emulsion includes a non-volatile oil, which is at least 50% by weight of a liquid UV agent. The composition also includes from about 10 to 25 wt % of substantially spherical starch particles, silicone elastomer particles, or a combination of these. The particles have a particle size of from about 2 to 40 microns. The weight ratio of the non-volatile oil to the particles is from about 1:10 to about 1:1. The composition is substantially free of glycerin and, optionally, includes from about 1 to 20 wt % of a volatile oil.

9 Claims, No Drawings

(56) References Cited

U.S. PATENT DOCUMENTS

| | | |
|---|---|---|
| 2014/0341823 A1 | 11/2014 | Alard |
| 2016/0346189 A1 | 12/2016 | Jansen et al. |
| 2018/0099164 A1 | 4/2018 | Jansen et al. |

FOREIGN PATENT DOCUMENTS

| | | |
|---|---|---|
| EP | 2382961 A2 | 11/2011 |
| EP | 1902704 B1 | 11/2013 |
| EP | 2823807 A1 | 1/2015 |
| FR | 2903306 | 6/2012 |
| FR | 2964562 B1 | 8/2012 |
| GB | 2423250 | 8/2006 |
| JP | H1059817 A | 3/1998 |
| JP | H11158036 A | 6/1999 |
| JP | 2002003338 A | 1/2002 |
| JP | 2003055134 A | 2/2003 |
| JP | 2003238356 A | 8/2003 |
| JP | 2003300831 | 10/2003 |
| JP | 2005200407 A | 7/2005 |
| JP | 2007269690 A | 10/2007 |
| WO | WO2002/092047 | 11/2002 |
| WO | WO2012168102 A2 | 12/2012 |
| WO | WO2013/088046 | 6/2013 |
| WO | WO2013/169506 A2 | 11/2013 |
| WO | WO2013/166342 A3 | 10/2014 |
| WO | WO2015108952 A1 | 7/2015 |

OTHER PUBLICATIONS

"The CIE 1976 Color Difference Formulas," *Color Research Applications*, vol. 2, pp. 7-11 (1977).

Todd, Charles, et al."Volatile Silicone Fluids for Cosmetics", vol. 91 Cosmetics and Toiletries pp. 27-32 (Jan. 1976).

Bartholomey et al., Colour and transparency for Ethnic makeup, South African Pharmaceutical & Cosmetic Review, Published Jan. 31, 2017.

Dow Corning DC 9506 Powder product information(date: Jul. 24, 2003).

International Search Report and Written Opinion of the International Searching Authority, PCT/US2015/011366, dated Apr. 30, 2015, 11 pages.

International Search Report and Written Opinion of the International Searching Authority, PCT/US2015/011367, dated Apr. 30, 2015, 11 pages.

International Search Report and Written Opinion of the International Searching Authority, PCT/US2015/011370, dated Apr. 30, 2015, 11 pages.

International Search Report and Written Opinion of the International Searching Authority, PCT/US2015/011372, dated Apr. 30, 2015, 10 pages.

International Search Report and Written Opinion of the International Searching Authority, PCT/US2015/011373, dated Apr. 14, 2015, 10 pages.

International Search Report and Written Opinion of the International Searching Authority, PCT/US2015/011374, dated Apr. 17, 2015, 11 pages.

International Search Report and Written Opinion of the International Searching Authority, PCT/US2015/041884, dated Sep. 16, 2015, 11 pages.

International Search Report and Written Opinion of the International Searching Authority, PCT/US2015/041886, dated Oct. 2, 2015, 10 pages.

Koboguard 5400 IDD published Jun. 2005 (2 pages).

Roussel et al., Glycerol as a skin barrier influencing humectant, Treatment of Dry Skin Syndrome, Chapter 32, pp. 473-480, 2012.

Takatoshi Sato, Tatsuya Ishida "Cosmetic Science" 4th ed. Sep. 20, 2001, Asakura Publishing Co., Ltd., p. 103-115.

Wang, The Property and Preparation of Organic Powder in Cosmetics, 2004 China Cosmetic Academic Symposium, pp. 306-310.

\* cited by examiner

COSMETIC COMPOSITION

FIELD OF THE INVENTION

The present disclosure relates generally to a cosmetic composition that helps improve the appearance and feel of human skin. More specifically, the present disclosure relates to a finisher composition comprising a UV agent that is applied as an overlying top layer to an underlying layer of skin care composition, thereby improving the look and feel of the treated skin.

BACKGROUND OF THE INVENTION

Personal care products are well known and widely used. These products have long been employed to protect, cleanse and moisturize, deliver actives, hide imperfections and reduce the oiliness and shine on keratinous surfaces. Personal care products have also been used to alter the color and appearance of skin and hair. A variety of personal-care compositions are available to provide skin care benefits and to help prevent and even counteract what many consumers consider to be undesirable "signs of skin aging" (e.g., fine lines, wrinkles, and uneven skin texture). Of these benefits, look and feel are generally considered to be the two most important and desired effects by consumers.

Traditionally, a wide variety of different functional materials are combined in a single skin care product in an attempt to deliver a range of look and/or feel benefits to consumers. For example, a conventional skin care product might contain skin actives such as humectants to improve the condition and health of the skin, emollients to lubricate the skin, powders to provide a skin feel and immediate skin appearance benefit, and/or UV actives to absorb skin damaging ultraviolet radiation ("UV").

Humectants are well known in the skin care industry, and may be incorporated into a personal care composition to provide a multitude of skin health and appearance benefits, such as increasing skin translucency (e.g., by less surface scattering and reducing refractive index gradients in the stratum corneum), reducing visible texture (e.g., by plumping of the stratum corneum) and generally improve skin function and strength. Glycerin is a commonly known humectant used widely in the field of cosmetics. It is not uncommon for glycerin to be incorporated into skin care compositions at relatively high levels to maximize the skin health benefit it provides. But glycerin is a relatively viscous, sticky material, and high levels of glycerin can feel undesirably sticky and heavy on the skin. Moreover, high levels of glycerin on the skin can make it look undesirably shiny and greasy, at least in part because glycerin is slow to absorb into the skin.

UV agents are also well known in the field of skin care compositions and impart a film that protects skin against the damaging effects of exposure to ultraviolet radiation from the sun. UV agents absorb and/or diffuse UV before it can interact with and damage skin. The ability of a composition to protect skin from UV is usually expressed as a sun protection factor ("SPF") rating. Combinations of UV agents are typically used in personal care compositions in order to raise the SPF rating of the composition and to offer broad spectrum protection for damaging UV (e.g., UV-A and UV-B). However, many UV agents (e.g., liquid UV agents and oil-soluble solid UV agents) are oily materials. Thus, while the ability of a sunscreen composition to protect skin from UV may be improved by adding UV agents, the resulting composition may have a heavy oily skin feel.

In some instances, particulate materials may be added to a personal care composition to address the undesirable skin feel and look properties imparted by one or more ingredients in the composition, such as glycerin or liquid UV actives. For example, micronized or spherical polymer particles may be used to provide feel, visible texture and/or wrinkle reduction benefits. Such particulate materials may provide an immediate visible texture (e.g., lines and wrinkles, pores, bumpy surface) reduction benefit to the skin by diffusely reflecting light, thereby providing a matting effect to the skin. In another example, particles may be added to a conventional skin care product to address the undesirable feel properties of a component ingredient such as glycerin (e.g., reduce the tacky feel). However, there are tradeoffs when attempting to increase these feel and look benefits. In some instances, the relatively high levels of powder required to provide the desired benefit may lead to products that are hard to spread on skin and/or products become noticeably white and can flake off the skin. In some instances, even incorporating relatively high amounts of powder may still fail to provide a suitable reduction in undesirable feel properties such as tackiness or oiliness. Further, some particulate materials may act as opacifying agents, which can turn the consumer product into make-up or make-up like product. While opacifying agents can provide a color benefit to a target skin surface, opacifying agents can also cause an increase in the visible texture of the skin, thus making undesirable textural features of the skin (e.g., wrinkles, pores, bumpy surface) more visible rather than hiding them.

Therefore, a need exists for a personal care composition that provides improved look and feel characteristics when used in conjunction with a conventional skin care composition. In particular, there remains a need for a personal care composition that improves the undesirable look and feel properties of a conventional skin care composition when applied as an overlying layer to one or more underlying base layer(s) of skin care compositions, which contain high levels of ingredients with undesirable feel and look properties, such as humectants and UV agents. There is also a need for a personal care composition that provides improved look and feel characteristics when used in conjunction with a conventional skin care composition and includes little or no pigments or colorants.

SUMMARY OF THE INVENTION

In order to address the problems of prior personal care compositions, disclosed herein is a personal care composition comprising from about 10 to 25 wt % of substantially spherical particles having a mean particle size of from about 2 to 40 microns; a non-volatile oil, wherein a weight ratio of non-volatile oil to silicone elastomer particles is from about 1:10 to about 1:1; from about 20 to 85 wt % of water; and, optionally, from about 1 to 20 wt % of a volatile oil. The composition is an oil-in-water emulsion, and the composition is substantially free of glycerin.

In some embodiments, the composition comprises from about 20 to 85 wt % of water and from about 10 to 25 wt % of substantially spherical particles selected from the group consisting of coated starch, uncoated starch, coated starch derivatives, uncoated starch derivatives, coated crosslinked starch, uncoated crosslinked starch, silicone elastomer particles, and combinations thereof. The particles have a mean particle size of from about 2 to 40 microns. The composition also comprises a liquid UV agent, wherein the liquid UV agent is present at an amount of at least 50% by weight of the non-volatile oil. The composition further includes less than 1 wt % of a pigment, and the composition has a contrast ratio of less than about 20 according to the Contrast Ratio method.

DETAILED DESCRIPTION

The finisher composition herein overcomes at least some of the issues of conventional personal care compositions. By applying the present finisher composition to an underlying personal care composition, the sticky, heavy feel caused by certain ingredients in the personal care composition may be reduced and the smooth, powdery feel of the powders is enhanced. Additionally, the appearance benefit provided by the powder materials in the finisher is increased.

Percentages are by weight of the personal care composition or the particular phase being described, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at ambient conditions, where "ambient conditions" means conditions at about 25° C., under about one atmosphere of pressure, and at about 50% relative humidity unless otherwise noted. As used in the description of the invention and the appended claims, the singular forms "a," "an," and "the" are intended to include the plural forms as well, unless the context clearly indicates otherwise.

Definitions

"Apply" or "application," as used in reference to a composition, means to apply or spread the composition onto a keratinous tissue surface.

"Derivative" refers to a molecule similar to that of another one, but differing from it in respect of a certain functional moiety. Derivatives may be formed by known reactive pathways. Suitable functional moieties include esters, ethers, amides, amines, carboxylic acids, hydroxyls, halogens, thiols, and/or salt derivatives of the relevant molecule.

"Free of" means that the stated ingredient has not been added to the composition. However, the stated ingredient may incidentally form as a byproduct or a reaction product of the other components of the composition. "Substantially free of" means that less than 3% (e.g., less than 1%, less than 0.5%, less than 0.25%, or even less than 0.1%) by weight of the composition of the stated ingredient has been added to the composition.

"Keratinous tissue" refers to keratin-containing layers disposed as the outermost protective covering of mammals which includes, but is not limited to, skin, hair, nails, cuticles, etc.

"Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 25° C.

"Personal care product" or "personal care composition" means a product or composition suitable for topical application on mammalian keratinous tissue.

"Regulating skin condition" means improving skin appearance and/or feel, for example, by providing a benefit, such as a smoother appearance and/or feel. Herein, "improving skin condition" means effecting a visually and/or tactilely perceptible positive change in skin appearance and feel. The benefit may be a chronic or acute benefit and may include one or more of the following: reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Safe and effective amount" means an amount of a compound or composition sufficient to significantly induce a positive benefit, preferably a positive skin or feel benefit, including independently or in combinations the benefits disclosed herein, but low enough to avoid serious side effects (i.e., to provide a reasonable benefit to risk ratio, within the scope of sound judgment of the skilled artisan).

"Signs of skin aging" include, but are not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Skin" means the outermost protective covering of mammals that is composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

"Skin-care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin-care active" means a compound or combination of compounds that, when applied to skin, provide an acute and/or chronic benefit to skin or a type of cell commonly found therein. Skin-care actives may regulate and/or improve skin or its associated cells (e.g., improve skin elasticity; improve skin hydration; improve skin condition; and improve cell metabolism).

"Skin-care composition" means a composition that includes a skin-care active and regulates and/or improves skin condition.

"Skin-care product" as used herein refers to a product that includes a skin-care composition. Some nonlimiting examples of "skin-care products" include skin creams, moisturizers, lotions, and body washes.

"Topical application" means to apply or spread the compositions of the present invention onto the surface of the keratinous tissue.

"UV agent" means a material or composition recognized by a skilled artisan in the field of sunscreen formulation to be a dermatologic ally acceptable ultraviolet radiation absorbing and/or diffusing material. Such UV actives may be described as being UV-A and/or UV-B active agents. Approval by a regulatory agency is generally required for inclusion of UV agents in formulations intended for human use.

Composition

Conventional skin care products that include relatively high levels of humectants such as glycerin commonly have undesirable feel and look characteristics when applied to skin, such as greasy or sticky feel and/or shiny appearance. The addition of particulate materials to these conventional products may address some of the look and feel problems, but typically have drawbacks of their own. Surprisingly, it has been discovered that a powder system that includes substantially spherical particles and is formulated to be applied as an overlying layer to a skin care product, as described in more detail below, can deliver desirable levels of feel and look benefits without the tradeoffs associated with some conventional powder systems.

The personal care composition disclosed herein is a stand-alone product sometimes referred to as a "finisher" or "finisher composition." Finishers are generally recognized in the cosmetics industry as compositions that are applied as a topcoat (i.e., overlying layer) to a basecoat (i.e., underlying layer) of composition such as a skin care product. The present finisher may be used in conjunction with, for example, a moisturizer, conditioner, anti-aging product, skin-lightening product or other skin care product to improve the look and feel characteristics of such products. The finisher composition herein is intended to be applied as an overlying layer to an underlying layer of skin care product. In some instances, the present finisher may be used in conjunction with an "all-in-one" type skin care product (i.e., a product that includes a skin care active such as glycerin, a UV active and a powder system), or with a skin care product that does not include a powder system. As can be seen in the comparative examples below, simply incorporating a powder system into a skin care product may not sufficiently address the undesirable look and feel characteristics associated with one or more components in the product.

To provide the desired look benefit, the finisher compositions herein are formulated to have a chroma value of less than 10 (e.g., less than 6 or even less than 3), according to the Chroma method described in more detail below, and a Contrast Ratio (i.e., opacity) of less than 20 (e.g, less than 10 or even less than 6), according to the Contrast Ratio method described in more detail below. The chroma and contrast ratio of the composition is controlled at least in part by controlling the type, amount and particle size of the powders in the finisher composition. For example, in addition to providing a suitable type and amount of silicone elastomer powder, it is also important to limit the amount and type of pigment particles and/or non-spherical particles in the finisher composition to provide the desired chroma and contrast ratio.

The present finisher is an oil-in-water ("O/W") emulsion comprising a continuous aqueous phase and a dispersed oil phase. The finisher also includes a suitable powder, which can be present in either phase. In some instances, it may be desirable to disperse hydrophobic powder particles in the oil phase of the finisher composition. The aqueous phase of the present finisher composition includes water at an amount of from 20% to 85% (e.g., 30% to 80% or even from 40% to 75%) by weight of the composition. The aqueous phase may include components other than water, such as water-soluble moisturizing agents, conditioning agents, anti-microbials, humectants and other water-soluble skin care actives, to impart an increased benefit to skin.

Non-Volatile Oil

In order to improve the skin appearance benefits provided by the finisher and minimize any undesirable visible tradeoffs (e.g., whitening), the spherical particles herein are wetted with a non-volatile oil (i.e., coated, partially coated, or soaked). Accordingly, the oil phase of the finisher composition oil-in-water emulsion includes a non-volatile oil. It is important to ensure that the particles are wetted with the right amount of non-volatile oil. If the particles are applied to the target skin surface with too little non-volatile oil, the finisher may appear white, and thus any wrinkle or pore masking benefit provided by the finisher composition may be overshadowed by undesirable whiteness. On the other hand, if too much non-volatile oil is present, the skin may appear undesirably shiny, thus reducing or eliminating the skin textural masking benefit of the finisher (i.e., the ability of the finisher to help reduce the appearance of perceived skin flaws related to skin texture, such as wrinkles and pores). Accordingly, it is important to provide a suitable weight ratio of the non-volatile oil to the particles of between 1:10 and 1:1 (e.g., from 1:5 to 4:5 or even from 1:4 to 3:5).

The non-volatile oil present in the finisher composition should remain on the skin for a relatively long period of time after application (e.g., more than 2 hours, 4 hours, or even more than 8 hours) without significant evaporation or absorption into the skin. If the oil evaporates, as a volatile oil would, or is absorbed into the skin, unwetted particles may be left on the skin resulting in undesirable whiteness. In addition, it may be desirable to select a non-volatile oil with a low refractive index, since high refractive index oils tend to make the skin appear shiny, which may reduce or even eliminate the skin textural masking benefit of the finisher.

The liquid UV agent(s), which are described in more detail below are particularly suitable non-volatile oils for use in the present finisher compositions. However, the oil phase of the finisher may also include other non-volatile oils such as non-volatile silicone oils, hydrocarbon oils, amides, esters, ethers and mixtures of these. Some non-limiting examples of silicone and hydrocarbon non-volatile oils can be found in copending U.S. Ser. Nos. 14/245,230 and 14/245,241.

UV Agent

To provide UV protection, the current composition contains UV agents. There are many types of UV agents, but one particularly useful form is liquid UV agents. As used herein "liquid UV agent" means one or more UV agent(s) that is(are) liquid at room temperature. Liquid UV agents include UV agents that are generally recognized as being liquids by those skilled in the art of sunscreen formulation. Liquid UV agents also include oil-soluble solid UV agents that are dissolved in a non-volatile oil to form a UV absorbing/diffusing composition that is a liquid at room temperature. Liquid UV agents tend to be oily or oil-based materials, and are also non-volatile, which is important for the longevity of the finisher on the skin. Accordingly, the liquid UV agent can provide the benefit desired from the non-volatile oil (e.g., particle wetting and longevity) and a UV protection benefit. Thus, the liquid UV agent may be used as the non-volatile oil in the finisher composition in whole or in part. The non-volatile oil of the finisher composition herein includes a liquid UV agent at an amount of at least 50% (e.g., at least 60%, 70%, 80%, 90%, 95%, 97%, 99% or even 100%).

The UV agent(s) present in the composition(s) herein may be added to provide a desired sun protection factor. For example, a finisher composition herein may have a sun protection factor of 5 or more (e.g., 10, 15, 20, 25, 30, 35, 40, 50, 60, 70 80 90 or even up to 100) when used as intended on skin. The SPF of the finisher composition may range from 4 to 100, from 8 to 55, or even from 12 to 35, as desired.

Some nonlimiting examples of known UV agents include Benzophenone, Benzophenone-1, Benzophenone-2, Benzophenone-3 (oxybenzone), Benzophenone-4 (sulisobenzone), Benzophenone-5, Benzophenone-6, Benzophenone-7, Benzophenone-8, Benzophenone-9 (dioxybenzone), Benzophenone-10, Benzophenone-11, Benzophenone-12, Benzotriazolyl Dodecyl p-Cresol, 3-Benzylidene Camphor, Benzylidene Camphor Sulfonic Acid, Benzyl Salicylate, Bis-Ethylhexyloxyphenol Methoxyphenyl Triazine (bemotrizinol), Bomelone, Bumetrizole, Butyl Methoxydibenzoylmethane (avobenzone), Butyl PABA, Cinnamidopropyltrimonium Chloride, Cinoxate, DEA-Methoxycinnamate, Dibenzoxazoyl Naphthalene, Di-t-Butyl Hydroxybenzylidene Camphor, Diethylamino Hydroxybenzoyl Hexyl Benzoate, Diethylhexyl Butamido Triazone (iscotrizinol), Diisopropyl Ethyl Cinnamate, Diisopropyl Methyl Cinnamate, Di-Methoxycinnamidopropyl Ethyldimonium Chloride Ether, Dimethyl PABA Ethyl Cetearyldimonium Tosylate, Dimorpholinopyridazinone, Dimorpholinopryridazinone, Disodium Bisethylphenyl Triaminotriazine Stilbenedisulfonate, Disodium Distyrylbiphenyl Disulfonate, Disodium Phenyl Dibenzimidazole Tetrasulfonate, Drometrizole, Drometrizole Trisiloxane, Ethyl Dihydroxypropyl PABA, Ethyl Diisopropylcinnamate, Ethylhexyl Bis-Isopentylbenzoxazolylphenyl Melamine, Ethyl Dimethoxybenzylidene Dioxoimidazolidine Propionate, Ethylhexyl Dimethyl PABA, Ethylhexyl Methoxycinnamate (octinoxate), Ethylhexyl Methoxydibenzoylmethane, Ethylhexyl Salicylate (octisalate), Ethylhexyl Triazone (octyl triazone), Ethyl Methoxycinnamate, Ethyl PABA, Ethyl Urocanate, Etocrylene, 4-(2-Beta-Glucopyrano-siloxy) Propoxy-2-Hydroxybenzophenone, Glyceryl Ethylhexanoate Dimethoxycinnamate, Glyceryl PABA, Glycol Salicylate, Hexanediol Disalicylate, Homosalate, Isoamyl Cinnamate, Isoamyl p-Methoxycinnamate, Isopentyl Trimethoxycinnamate Trisiloxane, Isopropylbenzyl Salicylate, Isopropyl Dibenzoylmethane, Isopropyl Methoxy-cinnamate, Kaempferia Galanga Root Extract, Menthyl Anthranilate (meradimate), Menthyl Salicylate, Methoxycinnamidopropyl Hydroxysultaine, Methoxycinnamidopropyl Laurdimonium Tosylate, 4-Methylbenzylidene Camphor (enacamene), Methylene Bis-Benzotriazolyl Tetramethylbutylphenol (bisoctrizole), Octocrylene, Octrizole, PABA, PEG-25 PABA, Phenylbenzimidazole Sulfonic Acid (ensulizole), Polyacrylamidomethyl Benzylidene Camphor, Polyamide-2, Polyquaternium-59, Polysilicone-15 (diethylbenzylidene malonate dimethicone), Potassium Methoxy-cinnamate, Potassium Phenylbenzimidazole Sulfonate, Red Petrolatum, Sodium Benzotriazoyl Butylphenol Sulfonate, Sodium Phenylbenzimidazole Sulfonate, Sodium Urocanate, TEA-Phenylbenzimidazole Sulfonate, TEA-Salicylate, Terephthalylidene Dicamphor Sulfonic Acid (ecamsule), Tetrabutyl Phenyl Hydroxybenzoate, Titanium Dioxide, Urocanic Acid, Zinc Cerium Oxide, Zinc Oxide Some particularly suitable examples of UV agents that are generally recognized as being liquids are Ethylhexyl Dimethyl PABA, Ethylhexyl Methoxycinnamate (octinoxate), Ethylhexyl Salicylate (octisalate), Homosalate, Isoamyl p-Methoxycinnamate (amiloxate), Menthyl Anthranilate (meradimate), Octocrylene, Polysilicone-15 (diethylbenzylidene malonate dimethicone) and combinations of these.

Some particularly suitable examples of oil-soluble solid UV agents, which can be dissolved in a non-volatile oil such as one of the UV agents described above to form a liquid UV agent, are Benzophenone-3 (oxybenzone), Benzophenone-9 (dioxybenzone), Bis-Ethylhexyloxyphenol Methoxyphenyl Triazine (bemotrizinol), Butyl Methoxydibenzoylmethane (avobenzone), Diethyl amino Hydroxybenzoyl Hexyl Benzoate, Diethylhexyl Butamido Triazone (iscotrizinol), Drometrizole Trisiloxane, Ethylhexyl Triazone (octyl triazone), 4-Methylbenzylidene Camphor (enacamene) and combinations of these.

Powder System

The finisher composition herein includes a suitable powder system. The powder system provides a light diffusing effect that provides a smooth look to the skin that is often more natural looking than makeup. Alternatively or additionally, the powder system may provide a silky or lubricious feel that can offset the undesirable greasiness associated with oils and/or the undesirable tacky feel associated with some humectants. It is important for the powder system to include suitable level of powder particles. If too much powder is present, then the look and feel benefits provided by the finisher can level off or even start to decline. In particular, the powder may no longer remain evenly distributed on the skin surface, which can lead to undesirable whitening (e.g., because powders no longer remain wetted) and/or flaking from the skin (e.g., because the powders no longer suitably adhere to the rest of the product film). On the other hand, if too little powder is present in the finisher then the undesirable look and/or feel properties of the underlying skin care composition may not be altered as desired.

It is believed, without being limited by theory, that the size of the particles is also important for delivering visible texture benefits on skin. In particular, it is important that the particles are large enough to protrude from the dry film formed by the skin care product on the skin (i.e., at least a portion of each (or most) of the particle(s) extends out of the surface of the film). In this way, a "rough" film is created, which diffusely reflects light (i.e., creates a bumpy-looking surface) and reduces the surface area of the underlying skin care product film that can be contacted by a user's hand or other object (i.e., reduces the tacky and/or greasy feel of the skin care composition, etc.). But as particle size increases, the number of particles in the finisher composition decreases. For substantially spherical particles, the number of particles per unit volume is proportional to the inverse of the cube of the particle diameter. Thus, using relatively large particles at a fixed amount (i.e., weight percent) of powder in the product effectively reduces the number of particles that can be added. On the other hand, using smaller particles may increase the number of particles present in the finisher, but may not provide the desired "rough surface" to the product film because a smaller portion of each particle (or even no portion of the particle) extends above the surface of the dry product film. On average, the dry film thickness of a conventional skin care product, when used as intended, typically ranges between 1 and 6 microns. Consequently, it is important to ensure that the selected particle size is appropriate for the skin care product it is intended to be used with. Particle size can be determined by any suitable method known in the art, such as by using coulter-counter equipment or the ASTM Designation E20-85, titled "Standard Practice for Particle Size Analysis of Particulate Substances in the Range of 0.2 to 75 Micrometers by Optical Microscopy," ASTM Volume 14.02, 1993. The particle sizes disclosed herein are volume-weighted mean particle sizes.

The particles in the powder systems disclosed herein are substantially spherical (i.e., the majority or even all the particles in the finisher composition are spherical). It is believed, without being limited by theory, that spherical particles generally provide a more suitable product feel relative to non-spherical particles, at least in part because a spherical particle creates less drag and rolls more smoothly across a surface than a non-spherical particle. As used herein, "spherical" and "sphere" mean particles that have an aspect ratio (i.e., ratio of major axis to minor axis) of from 1:1 to 2:1, (e.g., 1:1 to 2:1, 1:1 to 1.6:1 or even 1:1 to 1.4:1). The shape of the particles may be determined by any suitable method known in the art (e.g., optical microscope or electron microscope and suitable image analysis software).

In some instances, the powder system may include spherical silicone elastomer particles. For example, the finisher may include from 10% to 25% by weight of spherical silicone elastomer particles (e.g., from 12% to 25% or even 14% to 20%) dispersed or suspended in a suitable carrier. The amount of silicone elastomer powder in the finisher is determined based on the particulate material being in neat form (i.e., not swollen in solvent). It may be desirable to provide spherical silicone elastomer particles that have no tackiness and a rubber hardness (as measured by Durometer A defined in JIS K 6253) in the range of 10 to 90, (e.g., 20 to 80 or even from 25 to 75). When the rubber hardness is less than 5, the resulting silicone particles tend to become agglomerated, and dispersion into primary particles can be difficult. In contrast, a rubber hardness in excess of 90 may invite loss of soft texture that undesirably affects the feel properties provided by the finisher. Suitable silicone particles can be prepared from a variety of silicone materials, i.e. organopolysiloxanes, including cured silicone rubbers and poly(organosilsesquioxane) resins. The silicone elastomer particles suitable herein may be coated or uncoated. For example, the silicone particles may include silicone resin-coated silicone rubber particles (e.g., silicone rubber particles with polyorganosilsesquioxane attached to their surface). Commercially available silicone particles suitable for use in the present invention include: KSP-100, -101, -102, -103, -104, and -105, all from Shin Etsu; and DC9506 and DC 9701 from Dow Corning.

The silicone elastomer particles herein may have a median particle size of from 2 µm to 40 µm, (e.g., from 4 µm to 30 µm or even from 5 µm to 15 µm). Of course, it is to be appreciated that the particle sizes disclosed herein may be readily adapted for use with thicker or thinner films without departing from the spirit and scope of the present invention.

In some instances, the present finisher may include from 10% to 25% by weight of spherical starch particles (e.g., from 15% to 25% or even 20%) dispersed or suspended in a suitable carrier. The starch particles suitable for use herein may be coated or uncoated (e.g., coated with a suitable silicone material). In some instances, the starch particles may be a coated or uncoated starch derivative. The starch particles herein may have a median particle size of from 5 µm to 30 µm, (e.g., from 8 µm to 25 µm or even from 10 µm to 20 µm). Some non-limiting examples of commercially available starch particles suitable for use herein are tapioca starch (available as Tapioca Pure from AkzoNobel), corn starch (available as Purity 21C from AkzoNobel), potato starch, glyceryl starch (available as Dry-Flo GS from AkzoNobel), aluminum starch octenylsuccinate (available as Mackaderm ASTO-Dry from Rhodia, Inc., and Dry-Flo PC from AkzoNobel), calcium starch octenylsuccinate (available as Skin Flow C from MGP Ingredients, Inc., and Mackaderm CSTO-Dry from Rhodia, Inc.), and polymethylsilsesquioxane coated tapioca starch (available as Dry-Flo TS from AkzoNobel).

Other Particles

In some instances, the finisher may, optionally, include other particles in addition to the spherical silicone elastomer and/or spherical starch particles herein. For example, the finisher may, optionally, include non-spherical particles (e.g., non-spherical silicone elastomer particles, mica, talc, clay). However, the finisher generally includes less than 4% of non-spherical particles (e.g., less than 3% or even less than 1%). When referring to non-spherical silicone elastomer particles, the indicated percentages are understood to refer to amount of dry elastomer, as opposed to the total amount of elastomer and solvent, used for example for storage and shipping. Exemplary non-spherical crosslinked siloxane elastomers include the CTFA (Cosmetic, Toiletry, and Fragrance Association *International Cosmetic Ingredient Dictionary and Handbook*, 11th ed.) designated dimethicone/vinyl dimethicone crosspolymers supplied by a variety of suppliers including Dow Corning™, General Electric™, Shin Etsu™ (KSG 15 and 16), and Grant Industries. Other exemplary non-emulsifying crosslinked siloxane elastomers include the CTFA designated dimethicone crosspolymers including Dow Corning™; e.g. DC 9040 and DC 9045 which are supplied as a 12.5% elastomers in cyclomethicone, and DC 9041 which is supplied as 16% elastomer in dimethicone).

Pigment

The amount of pigment present in the finisher composition should be kept relatively low in order to avoid the undesirable aesthetics associated with higher levels of pigment (e.g., whiteness, flaking and lower spreadability). Finisher compositions herein may generally include less than 1%, (e.g., less than 0.5% or even less than 0.1%) by weight of particles that impart chroma and/or opacity to the composition (e.g., pigment grade titanium dioxide or iron oxide). In some instances, the present finisher is free of pigment and/or other colorants (e.g., lakes and dyes). Exemplary pigments can be found the Personal Care Product Council's *International Cosmetic Ingredient Dictionary and Handbook*, Thirteenth Edition, 2010.

Other Optional Materials

The present finisher may also include one or more optional materials that are commonly used in personal care compositions, such as volatile oils, emulsifiers, thickeners, skin care actives, combinations of these and the like. In particular, it may be desirable in some instances to include a volatile oil at up to 20 wt % (e.g., from 5% to 20%). The volatile oil may be a volatile silicone, a volatile hydrocarbon oil or a combination of these.

Volatile silicones include cyclic and linear volatile silicones. A description of various volatile silicones is found in Todd, et al. "Volatile Silicone Fluids for Cosmetics", 91 Cosmetics and Toiletries 27-32 (1976). Suitable cyclic volatile silicones include cyclic dimethyl siloxane chains containing an average of from about 3 to about 5 silicon atoms, preferably from about 4 to about 5 silicon atoms. Exemplary cyclic volatile silicones of varying viscosities include Dow Corning DC 244, DC 245, DC 344, and DC 345; GE Silicones-OSi Specialties Volatile Silicone 7207 and Volatile Silicone 7158; and GE Silicones SF1202. Suitable volatile linear silicones include the polydimethylsiloxanes containing an average of from about 2 to about 8 silicon atoms. Exemplary linear volatile silicones include the Dow Corning DC 200 series with viscosities of 0.65 cst, 1.0 cst, and 2.0 cst. In certain embodiments, the linear volatile silicones generally have viscosities of less than or equal to about 4 centistokes at 25° C., and the cyclic materials generally have viscosities of less than about 6 centistokes at 25° C.

Some non-limiting examples of suitable volatile hydrocarbon oils include isododecane (e.g., Permethyl-99A which is available from Presperse Inc.), isodecane, and the C7-C8 through C12-C15 isoparaffins (e.g., Isopar Series available from Exxon Chemicals).

The finisher composition may optionally include a humectant such as glycerin. However, the amount of humectant present in the finisher composition should be low enough to enable the finisher to provide the desired look and feel benefit to the underlying skin product. In some instances, the optional humectant is present at an amount of less than 10% or even less than 5%. It may be desirable to formulate the finisher such that the finisher composition is free of or substantially free of humectants. An exemplary class of humectants is polyhydric alcohols such as polyalkylene glycols, alkylene polyols and derivatives of these (e.g., propylene glycol, dipropylene glycol, polypropylene glycol, polyethylene glycol and derivatives thereof; glycerin, sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); ethoxylated glycerine; and propoxylated glycerine).

Methods

Chroma

This method provides a suitable means for measuring the color properties of a film formed from a personal care composition. Herein, "chroma," describes color and color intensity. For the purposes of the present disclosure, color is defined according to a value on the well known CIELAB color system.

To measure the color of personal care composition, a substantially uniform film of the composition is first created on a standard background. The film is created by applying the product to a standard opacity chart such as Form N2A commercially available from Leneta Company of Manwah, N.J. or equivalent, of which the top half is black and the bottom half is white, and then spread on the black area of the opacity chart using a Bird film applicator with a thickness of approximately 250 μm (e.g., as commercially available from BYK Gardner of Columbia, Md., or the equivalent thereof).

The color (L, a, and b values) of the product film is then measured using a spectrophotometer with settings selected to exclude specular reflection. Chroma is measured by a vector having its origin at the intersection of the red-green and blue-yellow axes and extending outward into the color space defined by the horizontal and vertical axes of the CIELAB color system. The length of the vector represents the chroma, and the direction of the vector represents the hue. The shorter the vector, the less colored is the composition, and the lower the chroma.

Contrast Ratio

This method provides a suitable means for determining the opacity of a composition. To measure the contrast ratio of a composition, the composition is applied to a standard opacity chart (e.g., Form N2A, Leneta Company of Manwah, N.J.) and then spread to form a substantially uniform film using a Bird film applicator with a thickness of approximately 38 μm (e.g., as commercially available from BYK Gardner of Columbia, Md., or the equivalent thereof). The film is allowed to dry for 1 hour under conditions of 22° C.+/−1° C., 1 atm. Using a spectrophotometer with the settings selected to exclude specular reflection, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average}(Y black)}{\text{average}(Y white)} \times 100$$

Visual Attribute Test (VAT)

The visible attribute test (VAT) is a technical panel used to quantify visible benefits of the finisher compositions herein when applied to facial skin. Fifteen to thirty female panelists who are pre-screened to have moderate or higher baseline levels of facial attributes such as fine lines, wrinkles, bumpy surface texture, and pores participate in each VAT study. Two trained expert graders then grade various attributes on each panelist's face both at baseline and 10 minutes after application of 0.45 grams of product to one side of the face. Reductions in facial attributes are then calculated as pre-treatment grade minus the post-treatment grade, and the significance of the differences are determined using ANOVA procedures (Tukey's HSD test).

Table 1 below is a hypothetical data table representing typical VAT data calculations for bumpy surface texture

TABLE 1

| Panelist Number | Pre-Treatment Grade | Post-Treatment Grade | Delta (Pre Minus Post) |
|---|---|---|---|
| 1 | 3.65 | 3.15 | 0.5 |
| 2 | 3.5 | 2.95 | 0.55 |
| 3 | 4.1 | 3.2 | 0.9 |
| 4 | 4.5 | 3.85 | 0.65 |
| 5 | 3.7 | 2.8 | 0.9 |

The facial attributes evaluated by the expert graders include the following:

Bumpy Surface—Skin unevenness or roughness associated with a "pebbled" or an "orange peel" surface. Based on both the degree of roughness as defined as height and proximity and the percentage of the face covered by the surfaced appearance. Roughness and coverage are equally weighted in the final grade. The bumpy surface score should not include obviously raised moles.

Shine—Light reflection on the skin surface. This should include both natural and artificial (product driven and characterized by an oily, greasy look) appearance.

The expert graders rate each of the above attributes both pre- and post-treatment using the 5-point continuous line scale shown below:

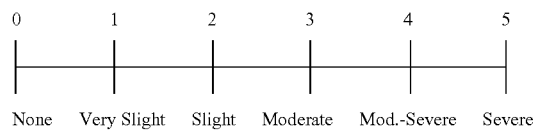

EXAMPLES

Examples 1-7

Representative Examples 1 to 7 illustrate finisher compositions according to the present disclosure. The compositions in Examples 1 to 7 are prepared in the following manner. In a suitable vessel, the water phase ingredients are combined and heated to 75° C. In a separate suitable vessel, the oil phase ingredients are combined and heated to 75° C. Next, the oil phase is added to the water phase and the resulting emulsion is milled (e.g., with a rotor-stator mill). The thickener is then added to the emulsion and the emulsion is cooled to 45° C. while stirring. At 45° C., the remaining additional ingredients are added. The product is then cooled with stirring to 30° C., milled again, and then poured into suitable containers.

Table 2 shows the ingredients used to make the composition of Examples 1-7, which utilize a silicone elastomer powder system.

TABLE 2

| | 1 | 2 | 3 | 4 | 5 | 6 | 7 |
|---|---|---|---|---|---|---|---|
| Water Phase: | | | | | | | |
| Water | qs | qs | qs | qs | qs | qs | qs |
| Disodium EDTA | 0.1 | 0.05 | 0.05 | 0.1 | 0.05 | 0.05 | 0.05 |
| Benzyl Alcohol | 0.5 | 0.5 | — | 0.5 | — | — | — |
| Methylparaben | 0.25 | 0.25 | — | 0.2 | — | — | — |
| Iodopropynyl Butylcarbamate | 0.09 | 0.09 | 0.09 | 0.09 | 0.09 | 0.09 | 0.09 |
| Phenylbenzimidazole Sulfonic Acid | 1.0 | — | — | 2.0 | — | — | — |
| Symdiol 68[1] | — | — | 0.7 | — | 0.7 | 0.7 | 0.7 |
| Phenoxyethanol | — | — | 0.5 | — | 0.5 | 0.5 | 0.5 |
| Oil Phase: | | | | | | | |
| Isopropyl Isostearate | 2.0 | 0.5 | — | 2.0 | — | — | — |
| Isopropyl lauroylsarcosinate | — | — | — | 3.0 | — | — | — |
| Octisalate | 4.0 | 4.5 | — | — | — | — | — |
| Homosalate | — | 4.0 | — | 8.0 | — | — | — |
| Octocrylene | 1.0 | 2.6 | — | 2.25 | — | — | — |
| Octinoxate | — | — | 4.0 | — | 4.0 | 7.5 | 4.0 |
| Avobenzone | 2.0 | 3.0 | 2.0 | 3.0 | 2.0 | 3.0 | 2.0 |
| Solastay S1[2] | — | — | 0.5 | — | — | 1.0 | — |
| Stearic Acid | 0.1 | 0.1 | 0.05 | 0.05 | 0.05 | 0.05 | — |
| Ethylparaben | 0.2 | 0.2 | — | 0.2 | — | — | — |
| Propylparaben | 0.15 | 0.15 | — | 0.15 | — | — | — |
| Cetyl alcohol | 0.5 | 0.5 | 0.3 | 0.4 | 0.3 | 0.3 | 0.3 |
| Stearyl alcohol | 0.5 | 0.5 | 0.4 | 0.4 | 0.4 | 0.4 | 0.4 |
| Behenyl alcohol | 0.5 | 0.5 | 0.4 | 0.3 | 0.4 | 0.4 | 0.4 |
| Cetearyl Glucoside | 0.4 | 0.4 | 0.2 | 0.2 | 0.2 | 0.2 | 0.2 |
| PEG-100 stearate | 0.2 | 0.3 | 0.2 | 0.2 | 0.2 | 0.2 | 0.2 |
| Thickener: | | | | | | | |
| Xanthan Gum | — | — | — | — | — | 0.1 | 0.1 |
| Carbopol Ultrez 10[3] | 0.2 | — | — | 0.2 | — | — | — |
| Simulgel INS-100[4] | — | 1.0 | — | — | — | — | — |
| Sepigel 305[5] | 1.0 | — | — | — | — | — | — |
| Makimousse-12[6] | — | — | 0.4 | — | 0.4 | 0.4 | 0.4 |
| Simulgel EG[7] | — | — | — | 2.25 | — | — | — |
| Powders: | | | | | | | |
| KSP 100[8] | — | 10.0 | — | 5.0 | 8.0 | — | 5.0 |
| KSP 101[9] | — | 5.0 | — | 5.0 | — | — | — |
| KSP 102[10] | 10.0 | — | — | — | — | 8.0 | — |

TABLE 2-continued

|  | 1 | 2 | 3 | 4 | 5 | 6 | 7 |
|---|---|---|---|---|---|---|---|
| KSP 103[11] | — | — | — | 5.0 | — | — | 3.0 |
| KSP 105[12] | — | — | 5.0 | 10.0 | — | 7.0 | 2.0 |
| DC 9506[13] | — | — | 5.0 | — | 3.0 | — | — |
| Total: | 100% | 100% | 100% | 100% | 100% | 100% | 100% |

[1] 1,2-hexanediol and caprylyl glycol, from Symrise
[2] Ethylhexyl Methoxycrylene, from Hallstar
[3] Carbomer, from Lubrizol
[4] Sodium acrylate/sodium acryloyldimethyl taurate copolymer, isohexadecane, and polysorbate 80, from Seppic
[5] Polyacrylamide, C13-14 isoparaffin, and laureth-7, from Seppic
[6] Sodium polyacrylate starch, from Kobo Products Inc.
[7] Sodium Acrylate/Sodium Acryloyldimethyl Taurate Copolymer & Isohexadecane & Polysorbate 80, from Seppic
[8] Vinyl dimethicone/methicone silsesquioxane crosspolymer, from Shin Etsu
[9] Vinyl dimethicone/methicone silsesquioxane crosspolymer, from Shin Etsu
[10] Vinyl dimethicone/methicone silsesquioxane crosspolymer, from Shin Etsu
[11] Vinyl dimethicone/methicone silsesquioxane crosspolymer, from Shin Etsu
[12] Vinyl dimethicone/methicone silsesquioxane crosspolymer, from Shin Etsu
[13] Dimethicone/vinyldimethicone crosspolymer, from Dow Corning

Examples 8-14

The compositions utilized in representative Examples 8 to 14 are prepared in generally the same manner as the compositions of Examples 1-7. Table 3 shows the ingredients used to make Examples 8-14, which utilize a starch powder system.

TABLE 3

|  | 8 | 9 | 10 | 11 | 12 | 13 | 14 |
|---|---|---|---|---|---|---|---|
| Water Phase: | | | | | | | |
| Water | qs | qs | qs | qs | qs | qs | qs |
| Disodium EDTA | 0.1 | 0.05 | 0.05 | 0.1 | 0.05 | 0.05 | 0.05 |
| Benzyl Alcohol | 0.5 | 0.5 | — | 0.5 | — | — | — |
| Methylparaben | 0.25 | 0.25 | — | 0.2 | — | — | — |
| Iodopropynyl Butylcarbamate | 0.09 | 0.09 | 0.09 | 0.09 | 0.09 | 0.09 | 0.09 |
| Phenylbenzimidazole Sulfonic Acid | 1.0 | — | — | 2.0 | — | — | — |
| Symdiol 68[1] | — | — | 0.7 | — | 0.7 | 0.7 | 0.7 |
| Phenoxyethanol | — | — | 0.5 | — | 0.5 | 0.5 | 0.5 |
| Oil Phase: | | | | | | | |
| Isopropyl Isostearate | 0.5 | 0.5 | — | 2.0 | — | — | — |
| Isopropyl lauroylsarcosinate | — | — | — | 3.0 | — | — | — |
| Octisalate | 4.0 | 4.5 | — | — | — | — | — |
| Homosalate | — | 4.0 | — | 8.0 | — | — | — |
| Octocrylene | 1.0 | 2.6 | — | 2.25 | — | — | — |
| Octinoxate | — | — | 4.0 | — | 4.0 | 7.5 | 4.0 |
| Avobenzone | 2.0 | 3.0 | 2.0 | 3.0 | 2.0 | 3.0 | 2.0 |
| Solastay S1[2] | — | — | 0.5 | — | — | 1.0 | — |
| Stearic Acid | 0.1 | 0.1 | 0.05 | 0.05 | 0.05 | 0.05 | — |
| Ethylparaben | 0.2 | 0.2 | — | 0.2 | — | — | — |
| Propylparaben | 0.15 | 0.15 | — | 0.15 | — | — | — |
| Cetyl alcohol | 0.5 | 0.5 | 0.3 | 0.4 | 0.3 | 0.3 | 0.3 |
| Stearyl alcohol | 0.5 | 0.5 | 0.4 | 0.4 | 0.4 | 0.4 | 0.4 |
| Behenyl alcohol | 0.5 | 0.5 | 0.4 | 0.3 | 0.4 | 0.4 | 0.4 |
| Cetearyl Glucoside | 0.4 | 0.4 | 0.2 | 0.2 | 0.2 | 0.2 | 0.2 |
| PEG-100 stearate | 0.2 | 0.3 | 0.2 | 0.2 | 0.2 | 0.2 | 0.2 |
| Thickener: | | | | | | | |
| Xanthan Gum | — | — | — | — | 0.1 | 0.2 | — |
| Carbopol Ultrez 10[3] | 0.2 | — | — | 0.2 | — | — | — |
| Simulgel INS-100[4] | — | 1.0 | — | — | — | — | — |
| Sepigel 305[5] | 1.0 | — | — | — | — | — | — |
| Makimousse-12[6] | — | — | 0.4 | — | 0.4 | 0.4 | 0.4 |
| Simulgel EG[7] | — | — | — | 2.25 | — | — | — |

TABLE 3-continued

|  | 8 | 9 | 10 | 11 | 12 | 13 | 14 |
|---|---|---|---|---|---|---|---|
| Powders: | | | | | | | |
| Dry Flo TS[8] | 15.0 | — | 10.0 | 20.0 | — | 10.0 | 9.0 |
| Tapioca Pure[9] | — | 15.0 | — | 5.0 | 2.0 | 5.0 | 6.0 |
| Dry Flo Pure[10] | — | — | 5.0 | — | 8.0 | 5.0 | — |
| Total: | 100% | 100% | 100% | 100% | 100% | 100% | 100% |

[1] 1,2-hexanediol and caprylyl glycol, from Symrise
[2] Ethylhexyl Methoxycrylene, from Hallstar
[3] Carbomer, from Lubrizol
[4] Sodium acrylate/sodium acryloyldimethyl taurate copolymer, isohexadecane, and polysorbate 80, from Seppic
[5] Polyacrylamide, C13-14 isoparaffin, and laureth-7, from Seppic
[6] Sodium polyacrylate starch, from Kobo Products Inc.
[7] Sodium Acrylate/Sodium Acryloyldimethyl Taurate Copolymer & Isohexadecane & Polysorbate 80, from Seppic
[8] Tapioca and polymethylsilsesquioxane, from Akzo Nobel
[9] Tapioca powder, from Akzo Nobel
[10] Aluminum Starch octenyl succinate, from Akzo Nobel Examples 15-21

The compositions utilized in representative Examples 15 to 21 are prepared in generally the same manner as the compositions of Examples 1-7. Table 4 shows the ingredients used to make the compositions of Examples 15-21, which utilize a combination of starch and silicone elastomer powder systems.

TABLE 4

|  | 15 | 16 | 17 | 18 | 19 | 20 | 21 |
|---|---|---|---|---|---|---|---|
| Water Phase: | | | | | | | |
| Water | qs | qs | qs | qs | qs | Qs | qs |
| Disodium EDTA | 0.1 | 0.05 | 0.05 | 0.1 | 0.05 | 0.05 | 0.05 |
| Benzyl Alcohol | 0.5 | 0.5 | — | 0.5 | — | — | — |
| Methylparaben | 0.25 | 0.25 | — | 0.2 | — | — | — |
| Iodopropynyl Butylcarbamate | 0.09 | 0.09 | 0.09 | 0.09 | 0.09 | 0.09 | 0.09 |
| Phenylbenzimidazole Sulfonic Acid | 1.0 | — | — | 2.0 | — | — | — |
| Symdiol 68[1] | — | — | 0.7 | — | 0.7 | 0.7 | 0.7 |
| Phenoxyethanol | — | — | 0.5 | — | 0.5 | 0.5 | 0.5 |
| Oil Phase: | | | | | | | |
| Isopropyl Isostearate | 2.0 | 0.5 | — | 2.0 | — | — | — |
| Isopropyl lauroylsarcosinate | — | — | — | 3.0 | — | — | — |
| Octisalate | 4.0 | 4.5 | — | — | — | — | — |
| Homosalate | — | 4.0 | — | 8.0 | — | — | — |
| Octocrylene | 1.0 | 2.6 | — | 2.25 | — | — | — |
| Octinoxate | — | — | 4.0 | — | 4.0 | 7.5 | 4.0 |
| Oxybenzone | — | — | — | — | — | — | — |
| Avobenzone | 2.0 | 3.0 | 2.0 | 3.0 | 2.0 | 3.0 | 2.0 |
| Solastay S1[2] | — | — | 0.5 | — | — | 1.0 | — |
| Stearic Acid | 0.1 | 0.1 | 0.05 | 0.05 | 0.05 | 0.05 | — |
| Ethylparaben | 0.2 | 0.2 | — | 0.2 | — | — | — |
| Propylparaben | 0.15 | 0.15 | — | 0.15 | — | — | — |
| Cetyl alcohol | 0.5 | 0.5 | 0.3 | 0.4 | 0.3 | 0.3 | 0.3 |
| Stearyl alcohol | 0.5 | 0.5 | 0.4 | 0.4 | 0.4 | 0.4 | 0.4 |
| Behenyl alcohol | 0.5 | 0.5 | 0.4 | 0.3 | 0.4 | 0.4 | 0.4 |
| Cetearyl Glucoside | 0.4 | 0.4 | 0.2 | 0.2 | 0.2 | 0.2 | 0.2 |
| PEG-100 stearate | 0.2 | 0.3 | 0.2 | 0.2 | 0.2 | 0.2 | 0.2 |
| Thickener: | | | | | | | |
| Xanthan Gum | — | — | 0.1 | — | — | — | — |
| Carbopol Ultrez 10[3] | 0.2 | — | 0.2 | — | — | — | — |
| Simulgel INS-100[4] | — | 1.0 | — | — | — | — | — |
| Sepigel 305[5] | 1.0 | — | — | — | — | — | — |
| Makimousse-12[6] | — | — | 0.4 | — | 0.4 | 0.4 | 0.4 |
| Simulgel EG[7] | — | — | — | 2.25 | — | — | — |
| Powders: | | | | | | | |
| Dry Flo TS[8] | — | — | 5.0 | 10.0 | — | 17.0 | — |
| Tapioca Pure[9] | 10.0 | — | — | — | 10.0 | — | — |
| Dry Flo Pure[10] | — | 10.0 | — | — | — | — | 10.0 |
| KSP 100[11] | — | 10.0 | — | — | 10.0 | 6.0 | — |
| KSP 101[12] | — | — | — | 6.0 | — | — | — |
| KSP 102[13] | — | — | — | — | — | — | 1.0 |
| KSP 103[14] | 5.0 | — | — | 4.0 | — | — | — |

TABLE 4-continued

|  | 15 | 16 | 17 | 18 | 19 | 20 | 21 |
|---|---|---|---|---|---|---|---|
| KSP 105[15] | — | — | 5.0 | — | — | — | 1.0 |
| DC 9506[16] | — | 5.0 | — | — | — | — | 3.0 |
| Total: | 100% | 100% | 100% | 100% | 100% | 100% | 100% |

[1]1,2-hexanediol and caprylyl glycol, from Symrise
[2]Ethylhexyl Methoxycrylene, from Hallstar
[3]Carbomer, from Lubrizol
[4]Sodium acrylate/sodium acryloyldimethyl taurate copolymer, isohexadecane, and polysorbate80, from Seppic
[5]Polyacrylamide, C13-14 isoparaffin, and laureth-7, from Seppic
[6]Sodium polyacrylate starch, from Kobo Products Inc.
[7]Sodium Acrylate/Sodium Acryloyldimethyl Taurate Copolymer & Isohexadecane & Polysorbate 80, from Seppic
[8]Tapioca and polymethylsilsesquioxane, from Akzo Nobel
[9]Tapioca powder, from Akzo Nobel
[10]Aluminum Starch octenyl succinate, from Akzo Nobel
[11]Vinyl dimethicone/methicone silsesquioxane crosspolymer, from Shin Etsu
[12]Vinyl dimethicone/methicone silsesquioxane crosspolymer, from Shin Etsu
[13]Vinyl dimethicone/methicone silsesquioxane crosspolymer, from Shin Etsu
[14]Vinyl dimethicone/methicone silsesquioxane crosspolymer, from Shin Etsu
[15]Vinyl dimethicone/methicone silsesquioxane crosspolymer, from Shin Etsu
[16]Dimethicone/vinyldimethicone crosspolymer, from Dow Corning Comparative Examples Examples 22-25: Improving the Appearance of a Facial Moisturizer The compositions of Examples 22-25 are prepared in generally the same manner as the composition of Examples 1-7. Table 5 shows the ingredients used in the compositions of Examples 22-25.

TABLE 5

|  | 22 Finisher A with 15% Elastomer | 23 Finisher A with 20% Starch | 24 Finisher B with 15% Elastomer | 25 Finisher B with 20% Starch |
|---|---|---|---|---|
| Water Phase: | | | | |
| Water | 74.224 | 69.224 | 70.33 | 65.33 |
| Disodium EDTA | 0.05 | 0.05 | 0.1 | 0.1 |
| Benzyl Alcohol | — | — | 0.5 | 0.5 |
| Methylparaben | — | — | 0.25 | 0.25 |
| Iodopropynyl Butylcarbamate | — | — | 0.09 | 0.09 |
| Phenylbenzimidazole Sulfonic Acid | — | — | 1.0 | 1.0 |
| Symdiol 68[1] | 0.8 | 0.8 | — | — |
| Phenoxyethanol | 0.376 | 0.376 | — | — |
| Oil Phase: | | | | |
| Isopropyl Isostearate | — | — | 1.33 | 1.33 |
| Octisalate | — | — | 4.0 | 4.0 |
| Octocrylene | — | — | 1.0 | 1.0 |
| Octinoxate | 4.0 | 4.0 | — | — |
| Avobenzone | 2.0 | 2.0 | 2.0 | 2.0 |
| Solastay S1[2] | 0.5 | 0.5 | — | — |
| Stearic Acid | 0.05 | 0.05 | 0.05 | 0.05 |
| Ethylparaben | — | — | 0.2 | 0.2 |
| Propylparaben | — | — | 0.15 | 0.15 |
| Cetyl alcohol | 0.3 | 0.3 | 0.3 | 0.3 |
| Stearyl alcohol | 0.4 | 0.4 | 0.4 | 0.4 |
| Behenyl alcohol | 0.4 | 0.4 | 0.4 | 0.4 |
| Cetearyl Glucoside | 0.2 | 0.2 | 0.2 | 0.2 |
| PEG-100 stearate | 0.2 | 0.2 | 0.1 | 0.1 |
| Thickener: | | | | |
| Carbopol Ultrez 10[3] | — | — | 0.2 | 0.2 |
| Simulgel INS-100[4] | 1.5 | 1.5 | 1.5 | 1.5 |
| pH Adjustor: | | | | |
| Triethanolamine | — | — | 0.9 | 0.9 |
| Powders: | | | | |
| Dry Flo TS[5] | — | 20.0 | — | 20.0 |
| KSP 100[6] | 15.0 | — | 15.0 | — |
| Total: | 100% | 100% | 100% | 100% |

[1]1,2-hexanediol and caprylyl glycol, from Symrise
[2]Ethylhexyl Methoxycrylene, from Hallstar
[3]Carbomer, from Lubrizol
[4]Sodium acrylate/sodium acryloyldimethyl taurate copolymer, isohexadecane, and polysorbate 80, from Seppic
[5]Tapioca and polymethylsilsesquioxane, from Akzo Nobel
[6]Vinyl dimethicone/methicone silsesquioxane crosspolymer, from Shin Etsu The compositions of Examples 22-25 were then placed in a Visual Attribute Test (VAT) to compare their effectiveness at reducing the appearance of various facial attributes. All of the examples were tested on top of Olay® Micro-Sculpting® brand facial moisturizing cream available from the Procter & Gamble Company, Cincinnati, Ohio. As can be seen from the results of this testing, summarized in Table 6 below, using the compositions of examples 22-25 on top of the facial moisturizer reduced the appearance attributes compared to using the facial moisturizer alone. Larger, positive VAT scores for bumpy surface and shine correspond to bigger visible reductions in the appearance of these attributes. Negative values indicate an increase in shine and/or bumpy surface.

TABLE 6

|  | Step 1 - FM Step 2 - Finisher A with 15% Elastomer | Step 1 - FM Step 2 - Finisher A with 20% Starch | Step 1 - FM Step 2 - Finisher B with 15% Elastomer | Step 1 - FM Step 2 - Finisher B with 20% Starch | FM Alone |
|---|---|---|---|---|---|
| Bumpy Surface | 0.23 | 0.27 | 0.23 | 0.25 | 0.06 |
| Shine | 0.18 | −0.05 | 0.15 | 0.03 | −0.50 |

Examples 26-29: Impact of Powders in UV Finishers

The compositions in Examples 26-29 are prepared in generally the same manner as the composition of Examples 1-7. Table 7 shows the ingredients used in the compositions of Examples 26-29.

TABLE 7

|  | 26<br>Finisher C<br>with 20%<br>Starch | 27<br>Finisher A<br>with No<br>Powder | 28<br>Finisher B<br>with No<br>Powder | 29<br>Finisher C<br>with No<br>Powder |
|---|---|---|---|---|
| Water Phase: | | | | |
| Water | 64.224 | 89.224 | 85.33 | 84.224 |
| Disodium EDTA | 0.05 | 0.05 | 0.1 | 0.05 |
| Benzyl Alcohol | — | — | 0.5 | — |
| Methylparaben | — | — | 0.25 | — |
| Iodopropynyl Butylcarbamate | — | — | 0.09 | — |
| Phenylbenzimidazole Sulfonic Acid | — | — | 1.0 | — |
| Symdiol 68[1] | 0.8 | 0.8 | — | 0.8 |
| Phenoxyethanol | 0.376 | 0.376 | — | 0.376 |
| Oil Phase: | | | | |
| Isopropyl Isostearate | — | — | 1.33 | — |
| Octisalate | — | — | 4.0 | — |
| Octocrylene | — | — | 1.0 | — |
| Octinoxate | 4.0 | 4.0 | — | 7.5 |
| Avobenzone | 2.0 | 2.0 | 2.0 | 3.0 |
| Solastay S1[2] | 0.5 | 0.5 | — | 1.0 |
| Stearic Acid | 0.05 | 0.05 | 0.05 | 0.05 |
| Ethylparaben | — | — | 0.2 | — |
| Propylparaben | — | — | 0.15 | — |
| Cetyl alcohol | 0.3 | 0.3 | 0.3 | 0.3 |
| Stearyl alcohol | 0.4 | 0.4 | 0.4 | 0.4 |
| Behenyl alcohol | 0.4 | 0.4 | 0.4 | 0.4 |
| Cetearyl Glucoside | 0.2 | 0.2 | 0.2 | 0.2 |
| PEG-100 stearate | 0.2 | 0.2 | 0.1 | 0.2 |
| Thickener: | | | | |
| Carbopol Ultrez 10[3] | — | — | 0.2 | — |
| Simulgel INS-100[4] | 1.5 | 1.5 | 1.5 | 1.5 |
| pH Adjustor: | | | | |
| Triethanolamine | — | — | 0.9 | — |
| Powders: | | | | |
| Dry Flo TS[5] | 20.0 | | | |
| Total: | 100% | 100% | 100% | 100% |

[1]1,2-hexanediol and caprylyl glycol, from Symrise
[2]Ethylhexyl Methoxycrylene, from Hallstar
[3]Carbomer, from Lubrizol
[4]Sodium acrylate/sodium acryloyldimethyl taurate copolymer, isohexadecane, and polysorbate 80, from Seppic
[5]Tapioca and polymethylsilsesquioxane, from Akzo Nobel The compositions of Examples 22-29 were then placed in a Visual Attribute Test (VAT) to compare their effectiveness at reducing the appearance of various facial attributes. All of the examples were tested on top of the Olay® Micro-Sculpting® brand facial moisturizing cream described above. As can be seen from the results of this testing, summarized in Tables 8, 9, and 10 below, using the compositions containing powders (Examples 22-26) on top of the facial moisturizer reduced the undesirable appearance attributes compared to using the compositions that did not contain powders (Examples 27-29).

TABLE 8

|  | Step 1 - FM<br>Step 2 - Finisher<br>A with<br>15% Elastomer<br>(Ex. 22) | Step 1 - FM<br>Step 2 - Finisher<br>A with<br>20% Starch<br>(Ex. 23) | Step 1 - FM<br>Step 2 - Finisher<br>A with<br>No Powder<br>(Ex. 27) |
|---|---|---|---|
| Bumpy Surface | 0.23 | 0.27 | −0.17 |
| Shine | 0.18 | −0.05 | −1.10 |

TABLE 9

|  | Step 1 - FM<br>Step 2 - Finisher<br>B with<br>15% Elastomer<br>(Ex. 24) | Step 1 - FM<br>Step 2 - Finisher<br>B with<br>20% Starch<br>(Ex. 25) | Step 1 - FM<br>Step 2 - Finisher<br>B with<br>No Powder<br>(Ex. 28) |
|---|---|---|---|
| Bumpy Surface | 0.23 | 0.25 | −0.13 |
| Shine | 0.15 | 0.03 | −1.33 |

TABLE 10

|  | Step 1 - FM<br>Step 2 - Finisher C<br>with 20% Starch<br>(Ex. 26) | Step 1 - FM<br>Step 2 - Finisher C<br>with No Powder<br>(Ex. 29) |
|---|---|---|
| Bumpy Surface | 0.16 | −0.26 |
| Shine | −0.06 | −1.68 |

Examples 30 and 31—Impact of Glycerin

Examples 30 and 31 demonstrate the undesirable effect of high levels of humectant on the appearance attributes of a skin care product. The compositions in Examples 30 and 31 contain the same high level of silicone elastomer particles and non-volatile silicone oil, and are otherwise identical except that Example 30 contains 5% glycerin while Example 31 contains 25% glycerin.

The compositions in Examples 30 and 31 are prepared by first combining the water phase ingredients and thickener in a container and mixing until uniform. The oil phase ingredients are combined in a separate container and mixed until uniform. The particulates are next added to the oil phase and the combination is mixed until uniform. Finally, the oil/particulate phase is added to the water phase and the resulting emulsion is subjected to high shear mixing (e.g., Flacktek Speedmixer, or rotor-stator mill) Table 11 shows the ingredients used in the compositions of Examples 30 and 31.

TABLE 11

|  | Example 30 | Example 31 |
|---|---|---|
| Water Phase: | | |
| Water | 20.84 | 0.84 |
| Glycerin | 5.0 | 25.0 |
| Disodium EDTA | 0.05 | 0.05 |
| Glydant Plus Liquid[1] | 0.3 | 0.3 |
| Niacinamide | 2.0 | 2.0 |
| D-panthenol | 0.5 | 0.5 |
| Laureth-4 | 0.2 | 0.2 |

TABLE 11-continued

|  | Example 30 | Example 31 |
|---|---|---|
| Thickener: | | |
| Simulgel INS-100[2] | 2.0 | 2.0 |
| Oil Phase: | | |
| Cyclomethicone D5 | 24.2 | 22.42 |
| Dimethicone 50 cst | 4.39 | 4.39 |
| DC9045[3] | 11.0 | 11.0 |
| Isopropyl lauroyl sarcosinate | 7.32 | 7.32 |
| Polysorbate 60 | 0.2 | 0.2 |
| Particles: | | |
| KSP 102[4] | 11.0 | 11.0 |
| KSP 105[5] | 11.0 | 11.0 |
| Total: | 100% | 100% |

[1]DMDM Hydantoin, Butane-1,3-diol, iodopropynyl butylcarbamate, water, from Lonza
[2]Sodium acrylate/sodium acryloyldimethyl taurate copolymer, isohexadecane, and polysorbate 60, from Seppic
[3]Cyclopentasiloxane and dimethicone crosspolymer, from Dow Corning
[4]Vinyl dimethicone/methicone silsesquioxane crosspolymer, from Shin Etsu
[5]Vinyl dimethicone/methicone silsesquioxane crosspolymer, from Shin Etsu The compositions of Examples 30 and 31 were then placed in a Visual Attribute Test (VAT) to compare their effectiveness at reducing the appearance of various undesirable facial attributes. As can be seen from the results of this testing, summarized in Table 12 below, increasing the level of glycerin from 5% to 25% significantly reduced the appearance attributes of these products in use. Larger VAT scores for bumpy surface and shine correspond to bigger visible reductions in the appearance of these attributes. Thus, these data clearly demonstrate the negative impact that high levels of glycerin can have on the appearance benefits of a skin care product.

TABLE 12

|  | Example 30 5% Glycerin | Example 31 25% Glycerin |
|---|---|---|
| Bumpy Surface | 0.29 | 0.09 |
| Shine | 0.23 | −0.16 |

Examples 32, 33 and 34: Impact of Layers

Examples 32, 33 and 34 compare the effects of combining a moisturizing composition (i.e., conventional skin care product) with a particulate composition in an "all-in-one" composition versus applying the present finisher composition as a standalone product to an underlying layer of a skin care composition in a two-step process.

Example 34 utilizes a finisher composition with a silicone elastomer powder system. The finisher composition is prepared by first combining the water phase ingredients and thickener in a container and mixing until uniform. The oil phase ingredients are combined in a separate container and mixed until uniform. The particulates are next added to the oil phase and the combination is mixed until uniform. Finally, the oil/particulate phase is added to the water phase and the resulting emulsion is subjected to high shear mixing (e.g., Flacktek Speedmixer, or rotor-stator mill). The "all-in-one" composition utilized in Example 32 is prepared in generally the same way as the compositions of Examples 30 and 31. The skin care composition of Example 33 is prepared by first combining the water phase ingredients and mixing until uniform, and warming if necessary. Next, the thickeners are added and the composition is again mixed until uniform. Finally, the pH adjustor, if present, is added and composition is mixed until uniform. The ingredients of each composition are shown below in Table 13.

TABLE 13

|  | Example 32 All-in-One | Example 33 First Layer No Powder | Example 34 Inventive Finisher |
|---|---|---|---|
| Water Phase: | | | |
| Water | 28.91 | 76.685 | 47.91 |
| Glycerin | 15.0 | 15.0 | — |
| Disodium EDTA | 0.05 | 0.025 | 0.05 |
| Symdiol 68[1] | 0.7 | 0.7 | 0.7 |
| Glycacil L[2] | 0.09 | 0.09 | 0.09 |
| Niacinamide | 5.0 | 5.0 | — |
| D-panthenol | 0.5 | 0.5 | — |
| Thickener: | | | |
| Simulgel INS-100[3] | 1.2 | 2.0 | 1.2 |
| Oil Phase: | | | |
| Cyclomethicone D5 | 24.0 | — | 20.0 |
| Dimethicone 50 cst | 3.75 | — | 3.75 |
| DC9045[4] | 5.5 | — | 11.0 |
| Laureth-4 | 0.3 | — | 0.3 |
| Particles: | | | |
| DC Elastomer[5] | 15.0 | — | 15.0 |
| Total: | 100% | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium acrylate/sodium acryloyldimethyl taurate copolymer, isohexadecane, and polysorbate 60, from Seppic
[4]Cyclopentasiloxane and dimethicone crosspolymer, from Dow Corning
[5]Spherical silicone elastomer powder, from Dow Corning, mean particle size of 40 μm and mean hardness of 40 A The skin care composition in Example 32 is an all-in-one formulation that contains the same glycerin and skin active levels as the skin care composition of Example 33. The composition of Example 32 also includes the same powder system as Example 34.

The all-in-one composition above (Example 32) and the corresponding two step composition (Example 33+34) were placed in a Visual Attribute Test (VAT) to compare their effectiveness at reducing the appearance of various facial attributes. The results of this testing are shown below in Table 14. As can be seen in Table 14, the two step system provides significantly greater visible benefits than their corresponding all-in-one system, despite both systems using the same spherical silicone elastomer powder and non-volatile silicones. Thus, these results demonstrate the benefits of applying the present finisher over an underlying layer of a skin care product.

TABLE 14

|  | All-in-One Example 32 | Two-Step Examples 33 + 34 |
|---|---|---|
| Bumpy Surface | 0.20 | 0.42 |
| Shine | −0.04 | 0.08 |

Examples 35, 36 and 37: Impact of Non-volatile Oil to Powder Ratio

The finisher compositions in Examples 35, 36 and 37 utilize a starch powder system that contains 20% starch particles and 50 cst dimethicone. While a starch particle system is used in these examples, it is believed that the silicone elastomer powder system of the present invention will generally provide the same results. More importantly, these examples demonstrate the importance of providing a suitable non-volatile oil to powder ratio. A key difference between the compositions of Examples 35, 36 and 37 is the non-volatile oil to powder ratio. Additionally, a few very minor adjustments were made to these formulations to ensure that they had similar physical properties and stability, but these adjustments are not expected to impact product performance. Examples 35, 36 and 37 are prepared in generally the same manner as described above with regard to Example 34. Table 15 shows the ingredients used in Examples 35, 36, and 37 along with the ingredients used to make the base layer for this test.

TABLE 15

|  | Base Layer Composition | Example 35 | Example 36 | Example 37 |
|---|---|---|---|---|
| Water Phase: |  |  |  |  |
| Water | 76.685 | 49.36 | 44.36 | 40.56 |
| Disodium EDTA | 0.025 | .05 | 0.05 | 0.05 |
| Glycerin | 15.0 | — | — | — |
| Symdiol 68[1] | 0.7 | 0.7 | 0.7 | 0.7 |
| Glycacil L[2] | 0.09 | 0.09 | 0.09 | 0.09 |
| Niacinamide | 5.0 | — | — | — |
| D-panthenol | 0.5 | — | — | — |
| Thickener: |  |  |  |  |
| Simulgel INS-100[3] | 2.0 | 1.5 | 1.5 | 1.3 |
| Oil Phase: | — | — | — | — |
| Cyclomethicone D5 | — | 12.0 | 12.0 | 6.0 |
| Dimethicone 50 cst | — | 5.0 | 10.0 | 20.0 |
| DC9045[4] | — | 11.0 | 11.0 | 11.0 |
| Laureth-4 | — | 0.3 | 0.3 | 0.3 |
| Particles: |  |  |  |  |
| Dry Flo TS[5] | — | 20.0 | 20.0 | 20.0 |
| Total: | 100% | 100% | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium acrylate/sodium acryloyldimethyl taurate copolymer, isohexadecane, and polysorbate 60, from Seppic
[4]Cyclopentasiloxane and dimethicone crosspolymer, from Dow Corning
[5]Tapioca and polymethylsilsesquioxane, from Akzo Nobel The compositions in Examples 35, 36, and 37 were placed in a VAT study as part of a two-step process, using the base layer in Table 15 as the underlying skin care product for each test. As can be seen from the results of this testing, summarized in Table 16 below, as the non-volatile oil-to-powder ratio increased, the appearance attributes provided by these compositions worsened. Thus, this data clearly shows the benefit of the preferred non-volatile oil to powder ratio in the finisher compositions herein.

TABLE 16

|  | Base Layer + Example 35 | Base Layer + Example 36 | Base Layer + Example 37 |
|---|---|---|---|
| Non-Volatile Oil to Powder Ratio | 1:4 | 1:2 | 1:1 |
| Bumpy Surface | 0.67 | 0.58 | 0.33 |
| Shine | 0.15 | 0.08 | −0.05 |

Example 38: Impact of Order of Layers

This example demonstrates the importance of applying a finisher as an overlying layer to an underlying layer of a skin care product, and not the other way around. The composition utilized in Example 38 is made by first combining the water phase ingredients and mixing until uniform. Next, the thickener is added and the composition is again mixed until uniform. Table 17 shows the ingredients used to make the composition in Example 38.

TABLE 17

|  | Example 38 |
|---|---|
| Water Phase: |  |
| Water | 78.16 |
| Glycerin | 15.0 |
| Disodium EDTA | 0.05 |
| Symdiol 68[1] | 0.7 |
| Glycacil L[2] | 0.09 |
| Niacinamide | 5.0 |
| D-panthenol | 0.5 |
| Thickener: |  |
| Makimousse-12[3] | 0.5 |
| Total: | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium polyacrylate starch, from Kobo Products Inc.

A VAT study was conducted using combinations of the composition of Example 38, the base layer composition shown in Table 15, and the finisher of Example 35 to understand the impact of the order in which the layers of the two step systems are applied to skin. Table 18 shows the two step systems placed in the VAT study. The intended order shown in Table 18 refers to the order wherein the skin care product is placed first, as the underlying layer, followed by placement of the finisher as the overlying layer. The reverse order refers to placement of the finisher first as the underlying layer, followed by placement of the skin care product as the overlying layer. Note that the base layer composition from Table 15 and the composition of Example 38 differ from one another only in the thickener used, and this difference is not expected to have a significant impact on the optical benefit demonstrated in this test.

TABLE 18

|  | Underlying Layer | Overlying Layer |
|---|---|---|
| Intended Order | Base Layer from Table 15 | Example 35 |
| Reverse Order | Example 35 | Example 38 |

As can be seen from the VAT results summarized in Table 19 below, applying the finisher as an overlying layer as intended delivers the desired benefits for the various visible attributes tested. However, applying the finisher as the underlying layer provided significantly less visible benefit. Thus, these results confirm the importance of the order of application steps of the current invention.

TABLE 19

|  | Reversed Order | Intended Order |
|---|---|---|
| Bumpy Surface | 0.28 | 0.67 |
| Shine | 0.00 | 0.15 |

Examples 39 and 40—Impact of Increased Opacity

The following two examples both contain the same high level of silicone elastomer spherical particles and non-volatile silicone oil, and are identical except that the composition of Example 40 contains 3.43% pigments while the composition of Example 39 does not contain pigments. The pigments used in Example 40 composition resulted in increased opacity compared to the composition of Example 39. Opacity is assessed by measuring contrast ratio (the higher the contrast ratio, the higher the level of opacity). The composition of Example 40 has a contrast ratio of 34, while the composition of Example 39 has a contrast ratio of 4.3. Examples 39 and 40 are prepared generally the same way as the composition of Examples 30 and 31 above. Table 20 below shows the ingredients used to make the compositions of Examples 39 and 40.

TABLE 20

|  | Example 39 | Example 40 |
|---|---|---|
| Water Phase: | | |
| Water | 21.04 | 21.04 |
| Glycerin | 5.0 | 5.0 |
| Disodium EDTA | 0.05 | 0.05 |
| Glydant Plus Liquid[1] | 0.3 | 0.3 |
| Niacinamide | 2.0 | 2.0 |
| D-panthenol | 0.5 | 0.5 |
| Thickener: | | |
| Simulgel INS-100[2] | 2.0 | 2.0 |
| Oil Phase: | | |
| Cyclomethicone D5 | 24.2 | 20.77 |
| Dimethicone 50 cst | 4.39 | 4.39 |
| DC9045[3] | 11.0 | 11.0 |
| Isononyl Isononanoate | 7.32 | 7.32 |
| Laureth-4 | 0.2 | 0.2 |
| Powders: | | |
| KSP 102[4] | 11.0 | 11.0 |
| KSP 105[5] | 11.0 | 11.0 |
| Pigments: | | |
| Titanium Dioxide[6] | — | 3.0 |
| Iron Oxides CI 77491[7] | — | 0.1 |
| Iron Oxides CI 77492[8] | — | 0.33 |
| Total: | 100% | 100% |

[1]DMDM Hydantoin, Butane-1,3-diol, iodopropynyl butylcarbamate, water, from Lonza
[2]Sodium acrylate/sodium acryloyldimethyl taurate copolymer, isohexadecane, and polysorbate 60, from Seppic
[3]Cyclopentasiloxane and dimethicone crosspolymer, from Dow Corning
[4]Vinyl dimethicone/methicone silsesquioxane crosspolymer, from Shin Etsu
[5]Vinyl dimethicone/methicone silsesquioxane crosspolymer, from Shin Etsu
[6]Titanium Dioxide, Isohexadecane, Polyhydroxystearic Acid, Triethoxycaprylylsilane
[7]Iron Oxides CI 77491, Cyclopentasiloxane, Methicone, PEG/PGG-18/18 Dimethicone
[8]Iron Oxides CI 77492, Cyclopentasiloxane, Methicone, PEG/PPG-18/18 Dimethicone The Example 39 and 40 compositions were then placed in a Visual Attribute Test (VAT) to compare their effectiveness at reducing the appearance of various facial attributes. Note that shine was not measured in this VAT, hence no shine results were reported. As can be seen from the results of this testing, summarized in Table 21 below, increasing opacity (higher contrast ratio) by using high refractive index pigments significantly reduced the optical benefit provided by the elastomer powder and silicone oil combination in these products. Thus, this data clearly demonstrates the negative impact that increased opacity has on the optical benefits of the powder and oil systems of the present invention.

TABLE 21

|  | Example 39 0% Pigment Contrast Ratio = 4.3 | Example 40 3.43% Pigment Contrast Ratio = 34 |
|---|---|---|
| Bumpy Surface | 0.65 | −0.03 |

Example 41, 42, 43, and 44: Particle Amount

These examples demonstrate the importance of including an appropriate amount of powder in the finisher. The compositions used in Example 41 to 44 are prepared generally the same way as described previously for these types of compositions. Table 22 shows the ingredients used to make the composition in Examples 41 to 44. While Examples 42, 43 and 44 include starch particles, it is believed that spherical silicone elastomer particles would yield substantially the same results.

TABLE 22

|  | Example 41 First Layer No Powder | Example 42 Finisher - 10% particles | Example 43 Finisher - 20% particles | Example 44 Finisher - 30% particles |
|---|---|---|---|---|
| Water Phase: | | | | |
| Water | 76.685 | 65.46 | 49.36 | 40.86 |
| Glycerin | 15.0 | | | |
| Disodium EDTA | 0.025 | 0.05 | 0.05 | 0.05 |
| Symdiol 68[1] | 0.7 | 0.7 | 0.7 | 0.7 |
| Glycacil L[2] | 0.09 | 0.09 | 0.09 | 0.09 |
| Niacinamide | 5.0 | — | — | — |
| D-panthenol | 0.5 | — | — | — |
| Thickener: | | | | |
| Simulgel INS-100[3] | 2.0 | 2.0 | 1.5 | 1.5 |
| Oil Phase: | | | | |
| Cyclomethicone D5 | — | 8.0 | 12.0 | 8.0 |
| Dimethicone 50 cst | — | 2.5 | 5.0 | 7.5 |
| DC9045[4] | — | 11.0 | 11.0 | 11.0 |
| Laureth-4 | — | 0.2 | 0.3 | 0.3 |
| Particles: | | | | |
| Dry Flo TS[5] | — | 10.0 | 20.0 | 30.0 |
| Total: | 100% | 100% | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium acrylate/sodium acryloyldimethyl taurate copolymer, isohexadecane, and polysorbate 60, from Seppic
[4]Cyclopentasiloxane and dimethicone crosspolymer, from Dow Corning
[5]Tapioca and polymethylsilsesquioxane, from Akzo Nobel Table 23 summarizes the result of the test. As seen in Table 23, the appearance benefit improves from 10% powder level to 20% powder level, but the worsens from 20% to 30% powder level.

TABLE 23

|  | Average VAT Score | | |
|---|---|---|---|
|  | 10% particles | 20% particles | 30% particles |
| Bumpy Surface | 0.43 | 0.67 | 0.52 |
| Shine | 0.02 | 0.15 | 0.10 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. In particular, U.S. Provisional Application Ser. Nos. 61/927,231, 61/927,236, 61/927,244 and 61/927,255 are incorporated herein by reference in their entirety. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A finisher composition in the form of an oil-in-water emulsion, the composition comprising:
   a) a continuous aqueous phase comprising about 20 to 85 wt. % of water, by weight of the composition;
   b) a dispersed oil phase that includes a non-volatile oil comprising a liquid UV agent, the liquid UV agent being present at 50% by weight of the dispersed oil phase;
   c) about 10 to 25 wt. % of substantially spherical starch particles having a mean particle size of about 5 to 30 microns, wherein a weight ratio of the liquid UV agent to the starch particles is about 1:10 to about 3:5;
   d) optionally, about 1 to 20 wt. % of a volatile oil;
   e) wherein the composition is substantially free of glycerin, comprises less than 1% by weight of pigment particles, has a chroma of less than about 10 according to the Chroma Method, and has a contrast ratio of less than about 20.

2. The finisher composition of claim 1, wherein the weight ratio of the non-volatile oil to the particles is from about 1:5 to about 3:5.

3. The finisher composition of claim 2, wherein the weight ratio of the non-volatile oil to the particles is from about 1:4 to about 3:5.

4. The finisher composition of claim 1, where the liquid UV agent further comprises an oil soluble solid UV agent.

5. The finisher composition of claim 1, wherein the liquid UV agent is present at more than 60% by weight of the dispersed oil phase.

6. The finisher composition of claim 5, wherein the liquid UV agent is present at an amount of at least 80% by weight of the dispersed oil phase.

7. The finisher composition of claim 1, wherein the liquid UV agent is selected from the group consisting of Ethylhexyl Dimethyl PABA, Ethylhexyl Methoxycinnamate (octinoxate), Ethylhexyl Salicylate (octisalate), Homosalate, Isoamyl p-Methoxycinnamate (amiloxate), Menthyl Anthranilate (meradimate), Octocrylene, Polysilicone-15 (diethylbenzylidene malonate dimethicone), Benzophenone-3 (oxybenzone), Benzophenone-9 (dioxybenzone), Bis-Ethylhexyloxyphenol Methoxyphenyl Triazine (bemotrizinol), Butyl Methoxydibenzoylmethane (avobenzone), Diethylamino Hydroxybenzoyl Hexyl Benzoate, Diethylhexyl Butamido Triazone (iscotrizinol), Drometrizole Trisiloxane, Ethylhexyl Triazone (octyl triazone), 4-Methylbenzylidene Camphor (enacamene) and combinations of these.

8. The finisher composition of claim 1, wherein the starch particles are present at an amount of from about 14 wt. % to about 20 wt. %.

9. The finisher composition of claim 1, wherein the composition is substantially free of humectants.

\* \* \* \* \*